United States Patent [19]
Denyer et al.

[11] Patent Number: 5,842,468
[45] Date of Patent: Dec. 1, 1998

[54] DOSIMETRIC SPACER FOR CALCULATING DOSAGE ADMINISTERED

[75] Inventors: Jonathan Stanley Harold Denyer, Pagham, United Kingdom; Kurt Verner Holger Nikander, Dalby, Sweden

[73] Assignees: Medic-Aid Limited, Pagham, Great Britain; Astra AB, Södertälje, Sweden

[21] Appl. No.: 817,950

[22] PCT Filed: Oct. 27, 1995

[86] PCT No.: PCT/EP95/04254

§ 371 Date: Jul. 14, 1997

§ 102(e) Date: Jul. 14, 1997

[87] PCT Pub. No.: WO96/13294

PCT Pub. Date: May 9, 1996

[30] Foreign Application Priority Data

Oct. 27, 1994 [GB] United Kingdom .................... 9421687

[51] Int. Cl.[6] .......................... A61M 11/00; A61M 16/10
[52] U.S. Cl. ................................ 128/200.23; 128/200.14; 128/203.12; 128/205.23
[58] Field of Search ......................... 128/202.22, 203.12, 128/200.23, 200.14, 205.23

[56] References Cited

U.S. PATENT DOCUMENTS

| | | | |
|---|---|---|---|
| 4,790,305 | 12/1988 | Zoltan et al. ...................... | 128/200.23 |
| 5,505,195 | 4/1996 | Wolf et al. .......................... | 128/203.15 |
| 5,709,202 | 1/1998 | Lloyd et al. ........................ | 128/200.23 |
| 5,743,252 | 4/1998 | Rubsamey et al. ................ | 128/200.23 |

*Primary Examiner*—Kimberly L. Asher
*Attorney, Agent, or Firm*—William A. Simons; Wiggin & Dana

[57] ABSTRACT

An apparatus for administering a fluid medicament to a patient in a gas for inhalation and for calculating the dosage administered to the patient comprising a holding member (1) for temporarily holding the medicament and gas prior to inhalation, means for introducing a quantity of the medicament into the holding chamber (1), a sensor (4) for detecting the introduction of the medicament into the holding chamber (1), detector means for detecting the rate of flow of gas inhaled by a patient from the holding chamber (1) and calculation means (25, 27, 29, 30, 31) operably connected to the sensor (4) and to the detector means for calculating the amount of medicament received by a patient. The calculating means (25, 27, 29, 30, 31) makes its calculation on the basis of the quantity of medicament released into the holding chamber (1), the volume of the holding chamber (1), the time elapsed from the detection of the introduction of the medicament, and the detected rate of flow of gas inhaled from the holding chamber (1). The calculation being made by assessing the concentration of the medicament in the holding chamber (1) on a time basis during reduction of the said concentration within the holding chamber (1), and be determining the volume of the gas received by the patient during inhalation, and the time elapsed from the detected introduction of medicament to the inhalation by the patient.

23 Claims, 6 Drawing Sheets

DOSIMETRIC SPACER FOR CALCULATING DOSAGE ADMINISTERED

The present invention relates to a method and apparatus for administering a measured dosage of fluid medicament to a patient in a gas for inhalation.

Throughout this specification and claims reference is made to a fluid medicament which may be a liquid or a powder in a fluidised form or in any other similar form.

Patient-operated multi-dose inhalers (MDI) are known having a mouthpiece through which a patient inhales. The patient must activate the MDI as he begins to inhale so that a metered dose of medicament is sprayed into a stream of air as it is sucked through the mouthpiece of the patient's inhalation.

Unfortunately the above MDI is often operated incorrectly so that much of the dose of medicament is wasted. The MDI must be activated or fired just as the patient begins to inhale so that the medicament is drawn deep into the periphery of the lungs where it is most effective. If the MDI is fixed too late, most of the medicament remains in the throat or bronchial tracts without any effect. Elderly patients and children are particularly likely to be unable to co-ordinate the firing of the MDI with the start of inhalation.

Some MDIs and dry powder inhalers (DPI) are available which include sensors which detect when a patient is inhaling and automatically activate the MDI. Whilst these MDIs and DPIs work well in detecting the commencement of inhalation in adults, elderly patients and children have difficulty in triggering the firing of the MDI since their inhalation flow rates are too small to be detected. Often, if a child or elderly patient is able to activate the MDI, this only occurs once their inhalation flow rate has increased to near its maximum, and triggering of the MDI therefore only occurs when the lungs of the patient are already half full.

MDIs and DPIs have been proposed which have a spacer chamber or holding chamber in conjunction with the MDI or DPI. When the MDI is activated, a dose of medicament is fired from the inhaler at high velocity. If a patient inhales the dose of medicament directly, then a large proportion of the dose will be impacted at the back of the throat due to the high velocity. Much of the dose does not reach the lungs where the medicament is intended to act. In some cases, less than fifty percent of the dose of medicament is deposited in the lungs. A particular problem with direct inhalation of the medicament by children is that they are often unable to inhale the full dose released due to the small volume of their lungs. The holding chamber may be disposed between the MDI and the patient. The medicament is sprayed into the holding chamber where it is held before the patient inhales from the holding chamber. The spacer chamber absorbs the high velocity of the medicament fired from the MDI and acts as a "buffer" chamber. The patient then inhales the dose at a much lower velocity. This can reduce the amount of the medicament impacting on the back of the throat by upwards of eighty percent, and may double the amount deposited in the lungs.

Furthermore, the use of a holding chamber means that, provided the medicament has already been fired into the holding chamber, the patient no longer needs to co-ordinate the firing with his inhalation.

The above proposal has some disadvantages. Although it is impossible to guarantee that a given dosage of medicament has actually reached deep into the patient's lungs, it is desirable to ensure that a dose as accurate as possible is given so that the patient's treatment is fully effective.

In the past, a dose of medicament has been sprayed into a holding chamber from which the patient has repeatedly inhaled until the whole of the dose is presumed to have been inhaled. Such a presumption is an inaccurate measurement of dose actually inhaled by the patient. Firstly, as the patient inhales, more air is drawn into the holding chamber to replace the air which is inhaled. This causes a dilution of the medicament within the holding chamber. Therefore, even when a patient has inhaled two or three times, medicament remains within the holding chamber. Secondly, the medicament sprayed into the holding chamber gradually settles on the walls and base of the holding chamber over time. This is caused in part by gravity, and in part by static charges on the medicament and on the holding chamber. Therefore, much of the medicament is not delivered to the patient during inhalation, no matter how many times he inhales.

It is an object of the present invention to reduce the above and other disadvantages, and in particular to accurately determine the dose of medicament received by the patient.

The scope of the present application is defined in the appended claims.

Embodiments of the present invention will now be described by way of example with reference to the drawings in which.

Figure 1:
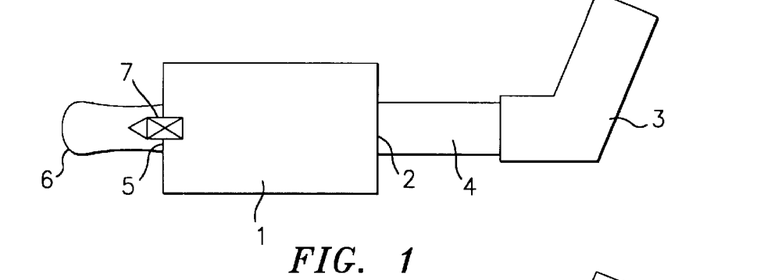
FIGS. 1 and 2 show a first embodiment of the present invention.

Referring to FIG. 1 a holding chamber 1 includes an inlet 2 through which a liquid medicament passes into the holding chamber from the multi-dose inhaler (MDI) 3. The MDI 3 releases the liquid medicament in a cloud of droplets. A sensor 4 is disposed between the MDI 3 and the holding chamber 1 which detects each actuation of the MDI 3. The sensor 4 also detects the rate at which air or other gas enters the holding chamber 1 via the inlet 2.

The holding chamber (also known as a spacer chamber or "buffer chamber") also includes an outlet 5 to which a mouthpiece 6 is attached. A patient inhales from the mouthpiece 6 drawing air or gas laden with medicament from the holding chamber 1. This causes more air or gas to be drawn into the holding chamber 1 through the inlet 2. The rate of flow of air through the inlet is detected by the sensor 4. A one way valve 7 is disposed between the outlet 5 and the mouthpiece 6 so that the patient can only inhale from the holding chamber 1 but cannot exhale into the holding chamber 1. The patient must remove the mouthpiece 6 from his mouth before exhaling.

Figure 2:
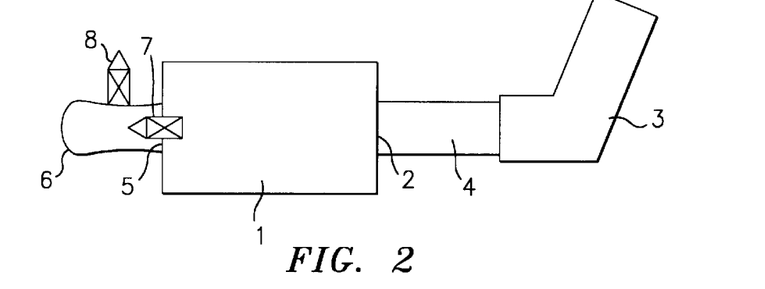

Referring to FIG. 2, a second one-way valve 8 is disposed in the mouthpiece 6 which permits exhaled air to be vented to atmosphere.

Once the medicament has been released into the holding chamber, the concentration of the medicament decreases, firstly as a result of deposition as the medicament settles on the walls and base of the holding chamber due to gravity and electrostatic forces between the walls of the holding chamber and the medicament. Secondly, the concentration decreases as a result of dilution caused by air entering the holding chamber to replace air inhaled by the patient.

Figure 3:
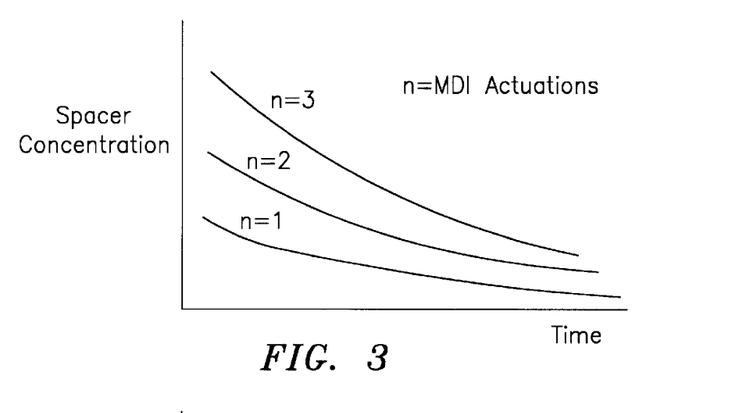
FIG. 3 shows how the concentration of the medicament varies over time in graphic form.
Figure 4:
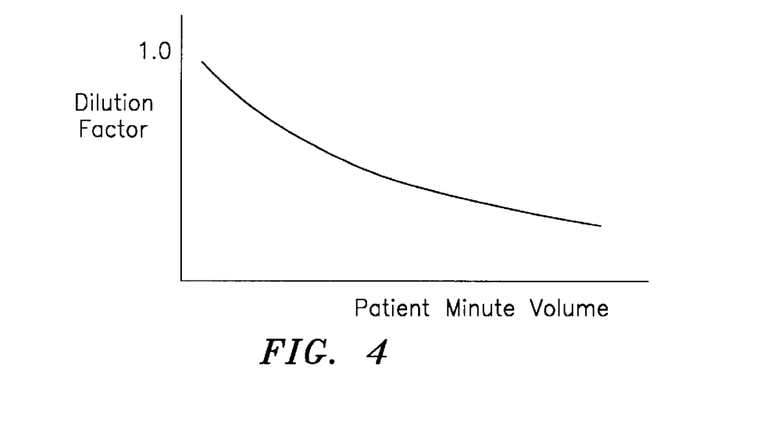
FIG. 4 shows the variation in dilution factor as the medicament is inhaled in graphic form.

Calculations must be carried out in order to determine the dose of medicament which has actually been delivered to the patient. To make these calculations, the following information must be known:

(i) the concentration of the medicament within the holding chamber 1 as shown in FIG. 3. This concentration depends on the number of actuations of the MDI releasing the medicament into the holding chamber and on the amount of time between the release of the medicament into the holding chamber and the patient inhaling since the medicament sediments over time; and (ii) the dilution factor where the concentration of the medicament in the holding chamber 1 decreases each time the patient inhales since air or gas not containing medicament enters the holding chamber 1. This dilution is shown in FIG. 4.

From this information, the dose of medicament received by the patient is monitored, and an indication is given by the apparatus when the desired dose has been administered.

This indication may be audible or visual.

Figure 5:
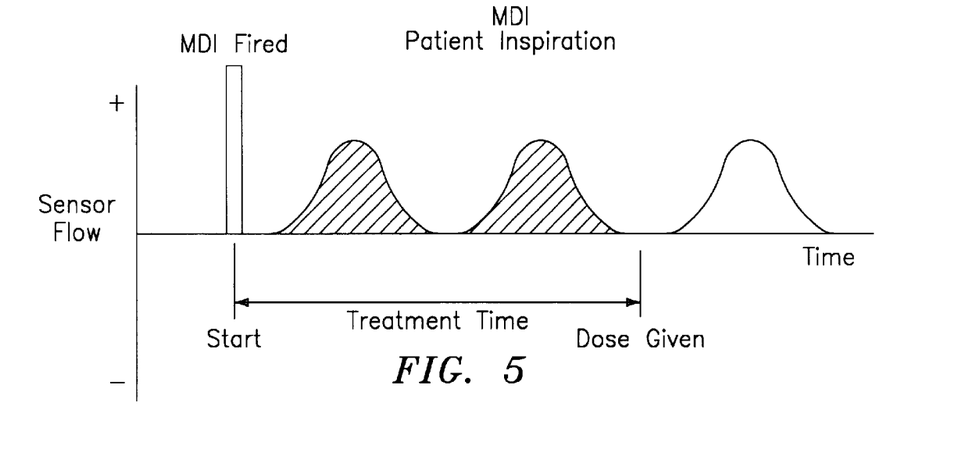
FIG. 5 shows graphically the flow through the sensor.

Referring to FIG. 5 the detected flow pattern through the inlet 2 of the holding chamber 1 is shown. Treatment starts upon firing of the MDI whereafter the inhalation of the patient is detected. The rate of inhalation is detected so that the calculations may be made to determine at what point the desired dose has been given. This point can then be indicated.

Calculation of the dose given to the patient shall now be described in connection with the embodiment shown in FIG. 2. The patient firstly connects the MDI 3 to the inlet port 2. The MDI 3 is fired to release a cloud of medicament into the holding chamber 1 past the sensor 4. The sensor 4, which might be a microphone or a pressure detector, detects the introduction of medicament into the holding chamber 1 and produces a signal. A data processor (not shown) receives the signal from the sensor 4 and starts a clock (not shown). The patient then puts the mouthpiece 6 to his mouth and inhales. Air and medicament within the holding chamber is drawn from the holding chamber through the port 5 and the mouthpiece. At the same time, air enters the holding chamber 1 through port 2 to replace the inhaled air, thereby causing dilution. The data processor calculates the amount of medicament delivered to the patient at very frequent intervals, typically every one hundredth of a second. In each of these sampled periods, the concentration of medicament within the holding chamber 1 is calculated to take account of the deposition of the medicament on the walls of the holding chamber 1 over time, and of the dilution effect of air entering the holding chamber 1 which does not carry any medicament. A memory contains a data look-up table which gives the concentration of medicament in the chamber at a time after the introduction of the medicament based on the deposition rate of the medicament. The memory also contains a data look-up table which gives the concentration of medicament in the chamber following the introduction of a set volume of air. The concentration of medicament within the holding chamber 1 is therefore calculated at the sampled time. The dose of medicament inhaled is then calculated by multiplying the volume of air sensed by the sensor during the sampled period by the concentration of medicament within the holding chamber at that sampled period. The dose calculated during this one sample period is then added to the dose calculated in calculations for previous sample periods. Once the cumulative total dose reaches a predetermined level, an indication is made to the patient that the full dose has been given. This might be indicated by a light or by an audible signal. The patient may require several breaths before the predetermined dose has been inhaled. The patient is able to exhale between inhalations through the mouthpiece since the one way valve 8 is able to vent the exhaled air to atmosphere.

The microprocessor must also count the number of actuations or firings of the MDI in order to calculate the initial concentration of medicament within the holding chamber 1. The calculation apparatus used in this embodiment is similar to the calculation apparatus described later in this specification in connection with FIGS. 15 and 16. However, in the present embodiment, in addition to the decrease in concentration caused by deposition of the medicament, the dilution must also be taken into account.

Figure 6:
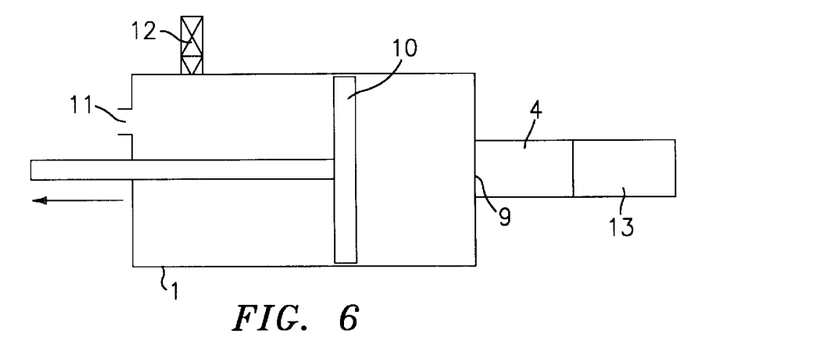
FIGS. 6 and 7 show a second embodiment of the present invention.

Referring now to FIG. 6, an alternative apparatus is shown which operates in conjunction with dry powder inhalers (DPI). DPIs are normally actuated by the patient's inspiratory flow. They are not suitable for patients with a very low inspiratory flow since the DPI is unlikely to be triggered reliably. Dry powder inhalers release the medicament in the form of a fine powder which is inhaled by a patient into their lungs. As with conventional MDIs, conventional DPIs suffer from the disadvantage that much of a given dose impacts with the back of a patient's throat. Referring to FIG. 6, a holding chamber 1 includes a first port 9 which is used both to load and empty the holding chamber 1. The holding chamber also includes a piston 10 movable within the chamber 1. As the piston 10 is drawn back, air or gas is sucked into the holding chamber 1 via the first port 9, and air trapped behind the piston escapes through a second port 11.

The holding chamber 1 includes a one way valve 12 which communicates with the gas or air loaded with medicament only when the piston 10 is pulled fully back. The one-way valve 12 permits air only to enter the buffer chamber.

Figure 7:
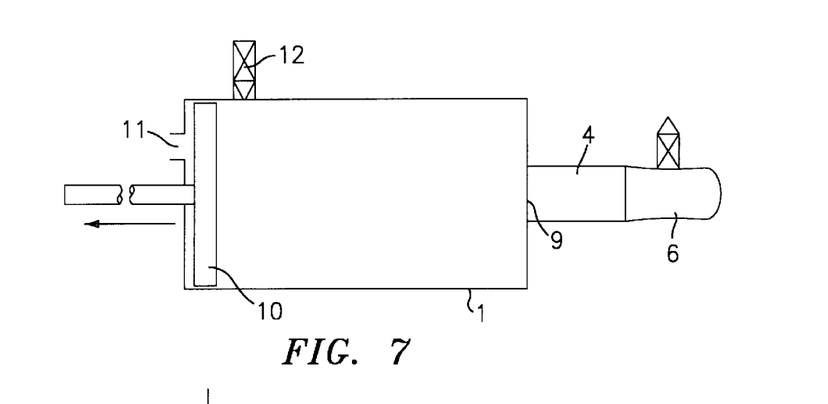
Figure 10:
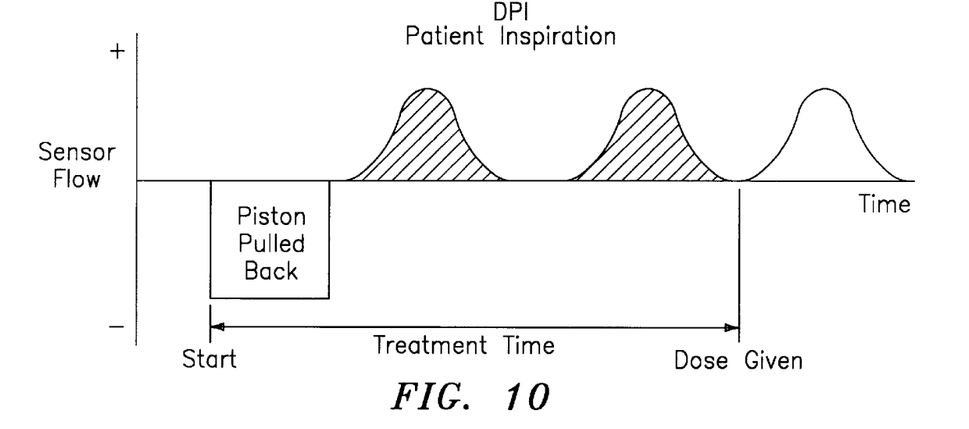

In use, the piston 10 is pulled back drawing air or gas into the holding chamber 1 through the first port 9. Before reaching the first port 9, the air or gas passes through a dry powder inhaler 13 which releases the medicament into the air or gas, and through a sensor 4. Once the piston 10 has been pulled back fully, it reveals the one-way valve 12. The piston 10 is fired in that position. The patient then removes the DPI 13 and replaces it with a mouthpiece 6 as shown in FIG. 7. The patient then inhales from the mouthpiece 6 and air or gas loaded with the medicament is sucked from the holding chamber passing through the port 9, through the sensor 4 and through the mouthpiece 6. The sensor 4 detects this airflow as shown in FIG. 10. Ambient air enters the buffer or holding chamber 1 through the one-way valve 12 in order to replace the air or gas being inhaled.

Figures 8, 9:
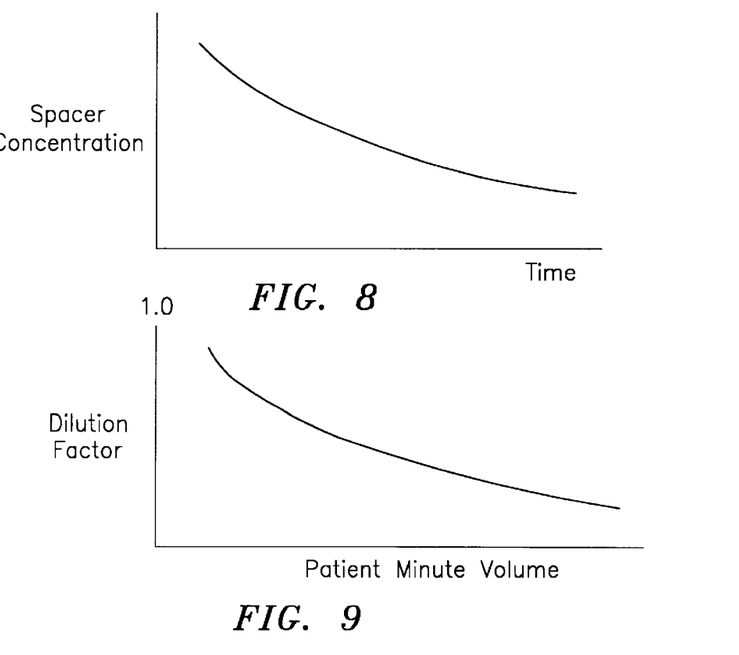
FIGS. 8, 9 and 10 show graphic characteristics of the second embodiment.

Calculations can again be made to accurately measure when a given dose of medicament has been administered. Again, it is necessary to know the concentration of the medicament within the holding chamber 1, as shown in FIG. 8, since sedimentation of medicament occurs over time. It is also necessary to know the dilution factor during inhalation as shown in FIG. 9. These can be calculated from the output of the sensor 4 as described in connection with FIG. 2.

Figure 11:
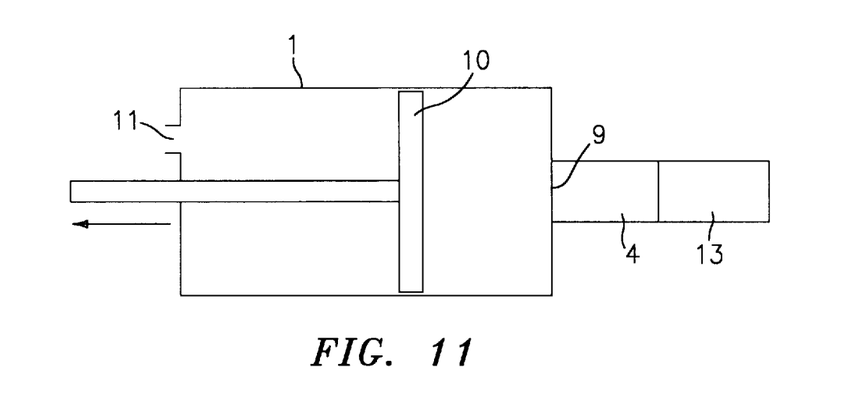
FIGS. 11 and 12 show a third embodiment of the present invention.
Figure 12:
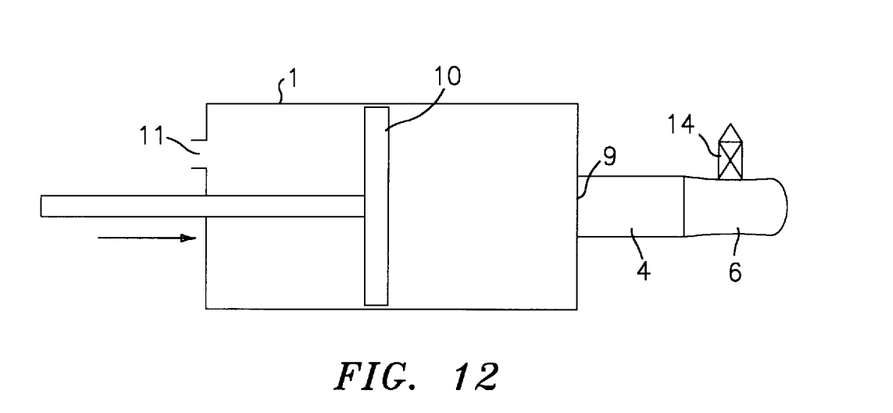

Once the correct dose has been administered, this is indicated. A further embodiment is shown in FIGS. 11 and 12 and, in this embodiment the piston 10 returns across the holding chamber 1 as the patient inhales. There is no one-way valve 12 in the holding chamber as in the previous embodiment. During inhalation and, consequently, emptying of the holding chamber 1, the piston is arranged to move only in the direction of emptying the holding chamber 1 to prevent dilution. To permit the patient to exhale, a one-way valve 14 is disposed in the mouthpiece 6.

Another advantage of this embodiment is that the dilution factor is eliminated, making dosage calculations simper, quicker and more accurate. No air enters the holding chamber 1 to replace the air or gas being inhaled since the piston moves to replace the inhaled air.

Calculation of the dose given to the patient shall now be described in connection with the embodiment shown in FIGS. 11 and 12. The patient firstly connects the DPI 13 to the port 9. The piston 10 is pulled back drawing air into the holding chamber 1 via the DPI 13 and the port 9. The sensor 4, which might be a microphone or a pressure detector, detects this introduction of medicament into the holding chamber 1 and products a signal. A data processor (not shown) receives the signal from the sensor 4 and starts a clock (not shown). The patient then removes the DPI from the port 9 and replaces it with a mouthpiece (FIG. 12). The patient inhales through the mouthpiece, and the air flows past the sensor 4. The data processor calculates the amount of medicament delivered to the patient very frequently, typically every one hundredth of a second. The concentration of medicament within the holding chamber 1 is continuously calculated to take account of the deposition of medicament on the walls of the holding chamber 1 over time. A memory contains a data look-up table which gives the concentration of medicament in the chamber 1 at a time after introduction of the medicament. The dose of medicament inhaled is then calculated by multiplying the volume of air sensed by the sensor by the concentration of medicament. The dose calculated during this one hundredth of a second sample period is then added to the dose calculated in calculations for previous sample periods. Once the cumulative total dose reaches a predetermined level, an indication is made to the patient that the full dose has been given. This might be indicated by a light or by an audible signal.

Figure 15:
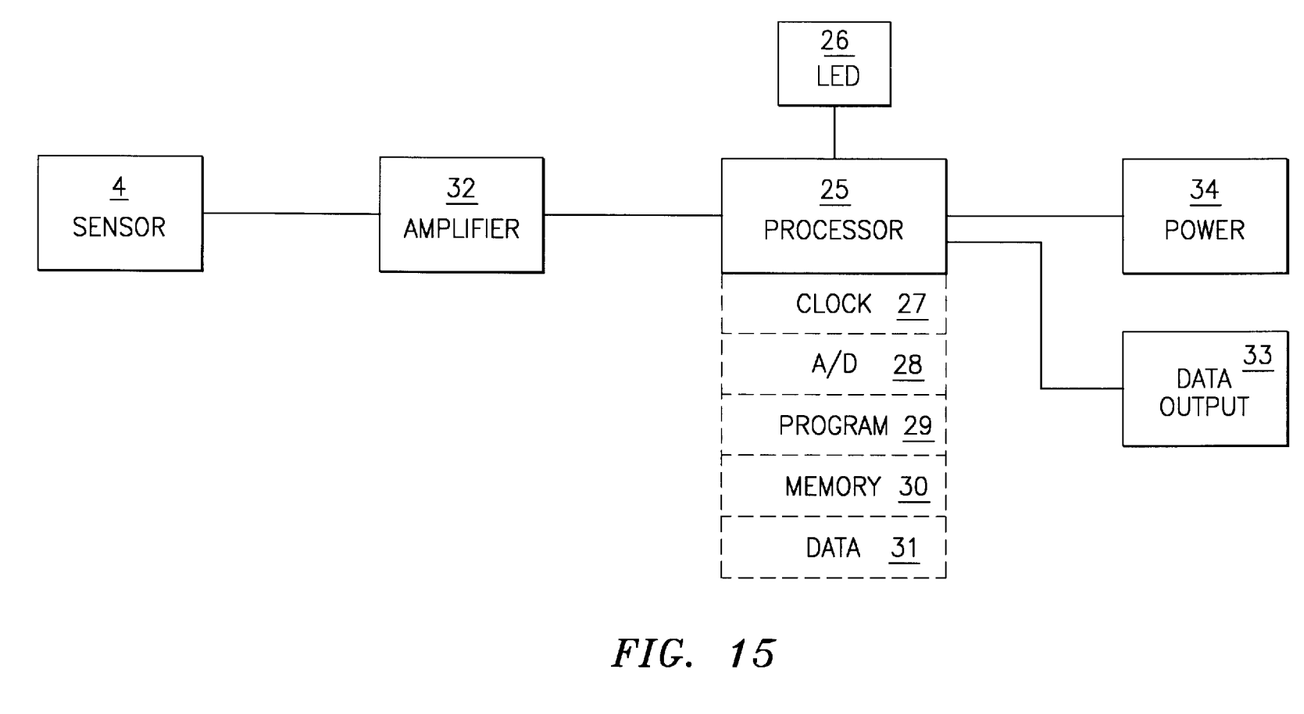
FIG. 15 shows a processor circuit for calculating the dose given to the patient.

FIG. 15 shows a block diagram of the processor system including a processor 25 powered by a power supply 34. The sensor 4 sends signals to the processor 25 via an amplifier 32 to indicate when the medicament is being introduced into the holding chamber 1, and the rate of inhalation of the patient. The processor 25 calculates the dose given to the patient on the basis of a program 29, a memory 30 containing look-up data 31, and a clock 27 and analog to digital converter (A/D) 28. Once the processor has calculated that the predetermined dose has been given, a signal is output via the data output 33.

Figure 13:
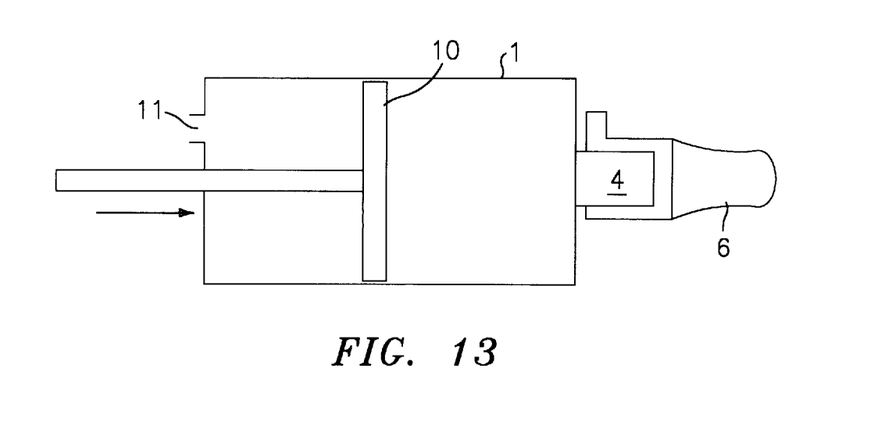
FIG. 13 shows a fourth embodiment of the present invention.
Figure 14:
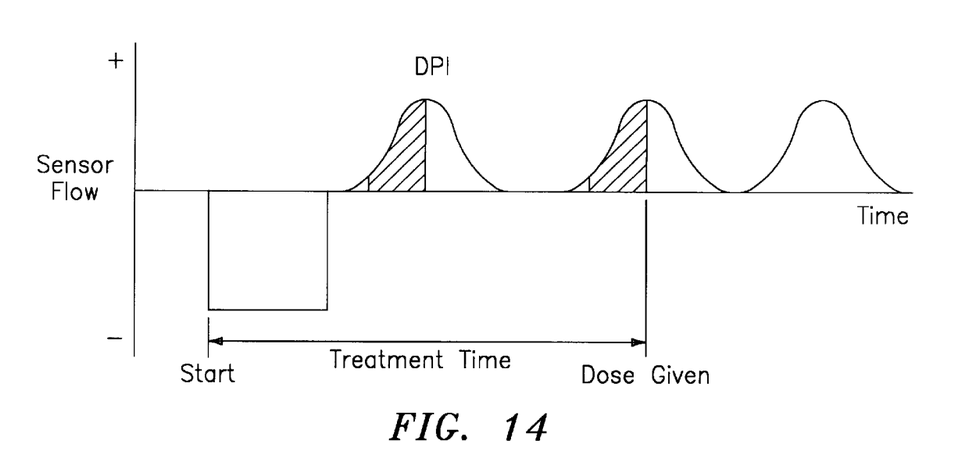
FIG. 14 shows graphically the flow of air or gas detected by the sensor.

Referring to FIGS. 13 and 14, the whole system may be controlled by movement of the piston 10. No valves are used, but the mouthpiece 6 includes two inlets, one from atmosphere and the other from the holding chamber 1. The sensor 4 detects when the patient is inhaling and exhaling. The piston 10 is automatically moved forwards when the patient inhales so that the patient inhales the air or gas containing medicament from the holding chamber 1. As with the earlier embodiments, an audible or visual warning can be given when the patient has received the correct dose.

Figure 16:
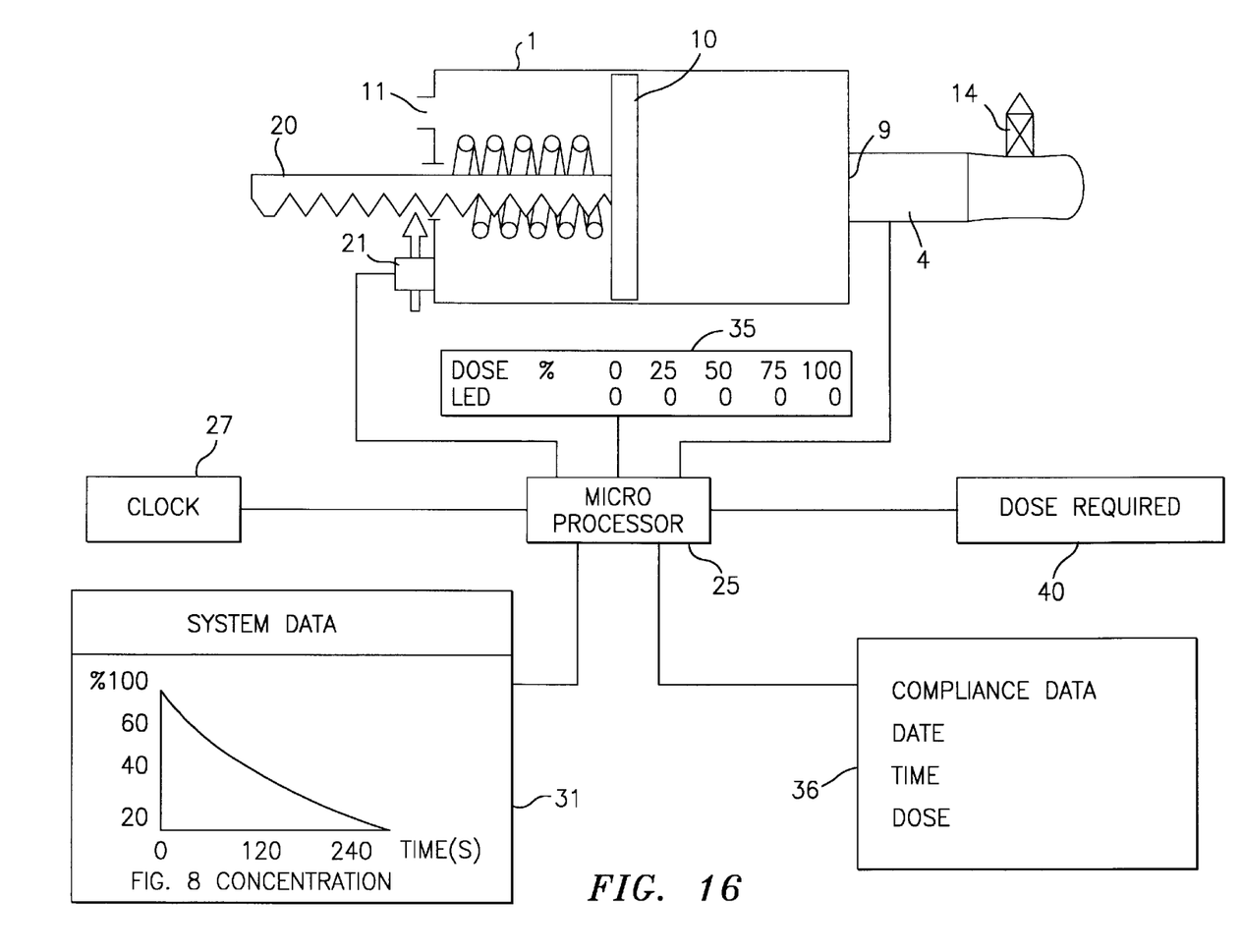
FIG. 16 shows a further embodiment of the present invention including control system.

In such an embodiment, once the piston has been withdrawn to fill the holding chamber 1 with medicament and air, biassing means may be used to biase the piston to push the air and medicament out of the holding chamber 1, and locking means for fixing the piston. The sensor 4 is a pressure sensor which senses the commencement of inhalation by a patient, and the microprocessor 25 releases the locking means to enable the piston to move through the holding chamber 1 in order to dispense sufficient air and medicament to satisfy the inhalation of the patient, before the locking means fixes the piston once the sensor 4 detects that the patient stopped inhaling. When the patient exhales, the exhaled breath is vented through the one way valve 14 in the mouthpiece. The inhalation process is repeated until the microprocessor determines that the predetermined dose has been administered at which point the patient is warned, and the locking means permanently fixes the piston so that no further medicament can be inhaled from the holding chamber 1. In a further embodiment, as shown in FIG. 16, a piston 10 is movable through a holding chamber 1 having a port 9 through which air and medicament is drawn from a DPI as the piston 10 is withdrawn. The piston 10 is withdrawn by a patient pulling a connecting rod 20. The connecting rod 20 is toothed, and a solenoid latch 21 is disposed just outside the holding chamber 1 which is engageable with the toothed connecting rod 20 to lock the piston 10. An optional spring 22 is disposed around the connecting rod 20 between the piston 10 and one end of the holding chamber 1 which biases the piston 10 to expel gas and medicament from the holding chamber 1. Furthermore, a dose panel 35 is included for indicating the proportion of the prescribed dose which has been administered. This embodiment operates in generally the same way as described above in connection with FIGS. 11, 12 and 15 in that the dose given to the patient is continuously monitored. The processor 25 uses the signal from the sensor 4, a clock signal from a clock 27, data on predetermined dose 40 and data 31 on how the concentration varies with time in the form of a look-up table. As the calculated dose given to the patient increases, LEDs on the dose panel 35 are illuminated corresponding to the proportion of the predetermined dose given, in this case a new LED is illuminated on each of 25%, 50%, 75% and 100%. Further, when the full predetermined dose has been administered, the microprocessor 25 drives the solenoid latch 21 to engage with the toothed connecting rod 20 to lock the piston 10. This prevents any further medicament being delivered to the patient. The microprocessor system also includes a compliance data memory 36 for recording the date, time and dose delivered which can subsequently be analyzed by a doctor.

Reference has been made above to look up tables which give data on how concentration of medicament decreases in time, and how concentration of medicament decreases by dilution caused by inhalation of known volumes. The data in the look-up tables must be gathered by experiment. For example, when the data for decrease in concentration of medicament with time is gathered, a known amount of medicament is introduced into the holding chamber, and the air in the holding chamber 1 is then expelled after a time into a filter paper. The expelled medicament is then weighed. This experiment is repeated for different time periods to establish the necessary data. The variation of concentration with time profile is likely to be different for different medicaments. Therefore the apparatus must have the correct profile programmed in.

The data of decrease in concentration of medicament with dilution is collected by introducing a known amount of medicament into the holding chamber, diluting the medicament by replacing some of the air, and then expelling the air and medicament into a filter paper. A profile can then be created.

In general, the holding chamber 1 would typically be of the order of 100–500 ml in volume, and the sensor 4 might be of the pressure type, such as a pneumatic, or of the turbulence-detecting type such as a microphone.

We claim:

1. Apparatus for administering a fluid medicament to a patient in a gas for inhalation and for calculating the dosage administered to the patient comprising a holding chamber for temporarily holding the medicament and gas prior to inhalation;

means for introducing a quantity of the medicament into the holding chamber;

a sensor for sensing the introduction of the medicament into the holding chamber;

detector means for detecting the rate of flow of gas inhaled by a patient from the holding chamber; and calculation means operably connected to the sensor and to the detector means for calculating the amount of medicament received by a patient on the basis of:

the preset quantity of medicament released into the holding chamber;

of the preset volume of the holding chamber;

the time elapsed from the sensing of the introduction of the medicament;

and of the detected rate of flow of gas inhaled from the holding chamber;

the calculation being made by assessing the concentration of the medicament in the holding chamber on a time basis during reduction of the said concentration within the holding chamber due at least in part to deposition of the medicament within the holding chamber, and by determining the volume of the gas received by the patient during inhalation, and the time elapsed from the sensed introduction of medicament to the inhalation by the patient.

2. Apparatus according to claim 1 including indication means for indicating that the measured dosage has been administered.

3. Apparatus for administering a fluid medicament to a patient in a gas for inhalation and for calculating the dosage administered to the patient comprising a holding chamber for holding the medicament and gas prior to inhalation;

means for introducing a quantity of the medicament into the holding chamber;

a sensor for sensing introduction of the medicament into the holding chamber;

detector means for detecting the rate of flow of gas inhaled by a patient from the holding chamber; and calculation means operably connected to the sensor and to the detector means for calculating the amount of medicament received by a patient, the calculation means including a timing means for indicating the time elapsed since the sensor senses the introduction of medicament into the holding chamber;

means for supplying the initial concentration of medicament in the holding chamber immediately after the introduction of medicament therein;

means for determining the concentration of medicament in the holding chamber during inhalation by the patient, the concentration of medicament reducing with time due at least in part to deposition of the medicament within the holding chamber, the determination being made on the basis of the initial concentration supplied by the means for supplying initial concentration, and of the time elapsed since the sensor sensed the introduction of medicament into the holding chamber; and means for determining the amount of medicament received by the patient by calculating the volume of gas inhaled by the patient from the holding chamber by integrating the rate of flow detected by the detector means, and by multiplying the calculated volume of gas by the concentration of medicament in the holding chamber at that time determined by the means for determining the concentration of medicament.

4. Apparatus according to claim 3 including a memory for storing a look-up chart showing the decrease of concentration of the medicament in the holding chamber over time.

5. Apparatus according to claim 4 wherein the means for determining the concentration of medicament in the holding chamber during inhalation makes the said determination also on the basis of the look-up chart in the memory.

6. Apparatus according to claim 3 wherein the means for supplying initial concentration of medicament in the holding chamber immediately after the introduction of medicament determines the said initial concentration on the basis of a preset quantity of medicament introduction into the holding chamber, and of a preset volume of the holding chamber.

7. Apparatus according to claim 3 wherein the holding chamber includes an inlet for permitting entry of gas into the holding chamber as gas is drawn out of the holding chamber by inhalation thereby causing a reduction of the concentration of medicament within the holding chamber by dilution.

8. Apparatus according to claim 7 wherein the means for determining the concentration of medicament in the holding chamber during inhalation makes the said determination also on the basis of the volume of gas previously inhaled by the patient.

9. Apparatus according to claim 7 including a memory for storing a look-up chart showing the decrease of concentration of the medicament in the holding chamber with the volume of air inhaled.

10. Apparatus according to claim 3 wherein the holding chamber includes a piston for reducing the volume of gas in the holding chamber as gas is inhaled, thereby preventing dilution.

11. Apparatus according to claim 10 including means for locking the piston.

12. Apparatus according to claim 11 wherein the means for locking the piston locks the piston upon administration of the measured dose.

13. Apparatus according to claim 10 wherein the piston is movable within the holding chamber for drawing gas and medicament into the holding chamber.

14. Apparatus according to claim 3 including a port in the holding chamber through which a quantity of medicament is introduced into the holding chamber by said releasing means, and through which gas is inhaled by a patient.

15. Apparatus according to claim 3 wherein the medicament is a cloud of liquid droplets.

16. Apparatus according to claim 3 wherein the medicament is a cloud of dry powder particles.

17. Apparatus according to claim 3 wherein the holding chamber includes a port through which the gas disposed in the chamber is inhaled, and through which the medicament is released into the holding chamber.

18. Apparatus according to claim 3 wherein the sensor for sensing introduction of medicament into the holding chamber and the detector means for detecting the rate of flow of gas inhaled by a patient from the holding chamber are constituted by a single sensor.

19. Apparatus according to claim 18 wherein the single sensor is disposed in the port of the holding chamber.

20. Apparatus for administering a fluid medicament to a patient in a gas for inhalation and for calculating the dosage administered to the patient comprising a holding chamber for temporarily holding the medicament and gas prior to inhalation;

means for introducing a quantity of the medicament into the holding chamber;

a sensor for sensing the introduction of the medicament into the holding chamber;

detector means for detecting the rate of flow of gas inhaled by a patient from the holding chamber; and calculation means operably connected to the sensor and to the detector means for calculating the amount of medicament received by a patient on the basis of:
the preset quantity of medicament released into the holding chamber;
of the preset volume of the holding chamber;
the time elapsed from the sensing of the introduction of the medicament, of the detected rate of flow of gas inhaled from the holding chamber;
the calculation being made by assessing the concentration of the medicament in the holding chamber on the basis of the detected inhaled volume during reduction of the said concentration within the holding chamber due at least in part to dilution of the medicament within the holding chamber, and by determining the volume of the gas received by the patient during inhalation.

21. Apparatus for administering a fluid medicament to a patient in a gas for inhalation and for calculating the dosage administered to the patient comprising a holding chamber for holding the medicament and gas prior to inhalation;

means for introducing a quantity of the medicament into the holding chamber;

a sensor for sensing introduction of the medicament into the holding chamber;

detector means for detecting the rate of flow of gas inhaled by a patient from the holding chamber; and calculation means operably connected to the sensor and to the detector means for calculating the amount of medicament received by a patient, the calculation means including
a timing means for indicating the time elapsed since the sensor senses the introduction of medicament into the holding chamber;
means for supplying the initial concentration of medicament into the holding chamber immediately after the introduction of medicament therein;
means for determining the concentration of medicament in the holding chamber during inhalation by the patient, the concentration of medicament reducing with the volume of gas inhaled due at least in part to dilution of the medicament within the holding chamber, the determination being made on the basis of the initial concentration supplied by the means for supplying initial concentration, and of the volume of gas inhaled, calculated from the rate of flow of gas detected by the detector since the sensor sensed the introduction of medicament into the holding chamber; and
means for determining the amount of medicament received by the patient by calculating the volume of gas inhaled by the patient from the holding chamber by integrating the rate of flow detected by the detector means, and by multiplying the calculated volume of gas by the concentration of medicament in the holding chamber at that time determined by the means for determining the concentration of medicament.

22. A method for administering a measured dosage of a fluid medicament to a patient in a gas for inhalation using an apparatus comprising:

a holding chamber for holding the medicament and gas prior to inhalation;

means for introducing a quantity of medicament into the holding chamber;

a sensor for sensing the introduction of medicament into the holding chamber;

detector means for detecting the rate of flow of gas inhaled by a patient from the holding chamber; and calculation means operably connected to the sensor and to the detector means for calculating the amount of medicament received by a patient;

the method comprising:
sensing the introduction of medicament into the holding chamber, the sensing being made by the sensor;
monitoring the time elapsed since the introduction of the medicament is sensed, the monitoring being made by the calculation means;
supplying the value of the initial concentration of medicament in the holding chamber;
determining the concentration of medicament in the holding chamber during inhalation by the patient, the concentration of medicament reducing with time due at least in part to deposition of the medicament within the holding chamber, the determination being made on the basis of the supplied initial concentration and of the time elapsed since the sensor senses the introduction of medicament into the holding chamber; and
determining the amount of medicament received by the patient by calculating the volume of gas inhaled by the patient from the holding chamber by integration of the rate of flow detected by the detector means, and by multiplying the calculated volume of gas by the determined concentration of medicament in the holding chamber at that time.

23. A method of administering a fluid medicament to a patient in a gas for inhalation and for calculating the dosage administered to the patient comprising sensing the introduction of a quantity of medicament into a holding chamber;

detecting the rate of flow of gas inhaled by a patient from the holding chamber;

monitoring the time elapsed from the sensing of the introduction of the quantity of medicament into the holding chamber;

determining the concentration of medicament in the holding chamber during inhalation by the patient, the concentration of medicament reducing with time due at least in part to deposition of the medicament within the holding chamber, the determination being made on the basis of the predetermined initial concentration of medicament within the holding chamber immediately after the introduction of medicament therein, and on the basis of the monitored time elapsed since the sensing of the introduction of medicament; and calculating the amount of medicament received by the patient by calculating the volume of gas inhaled by the patient from the holding chamber by integrating the detected rate of flow, and by multiplying the calculated volume of gas inhaled by the determined concentration of medicament in the holding chamber.

* * * * *